Nov. 23, 1976 D. L. ARMSTRONG Plant Pat. 3,983
ROSE PLANT
Filed November 18, 1975
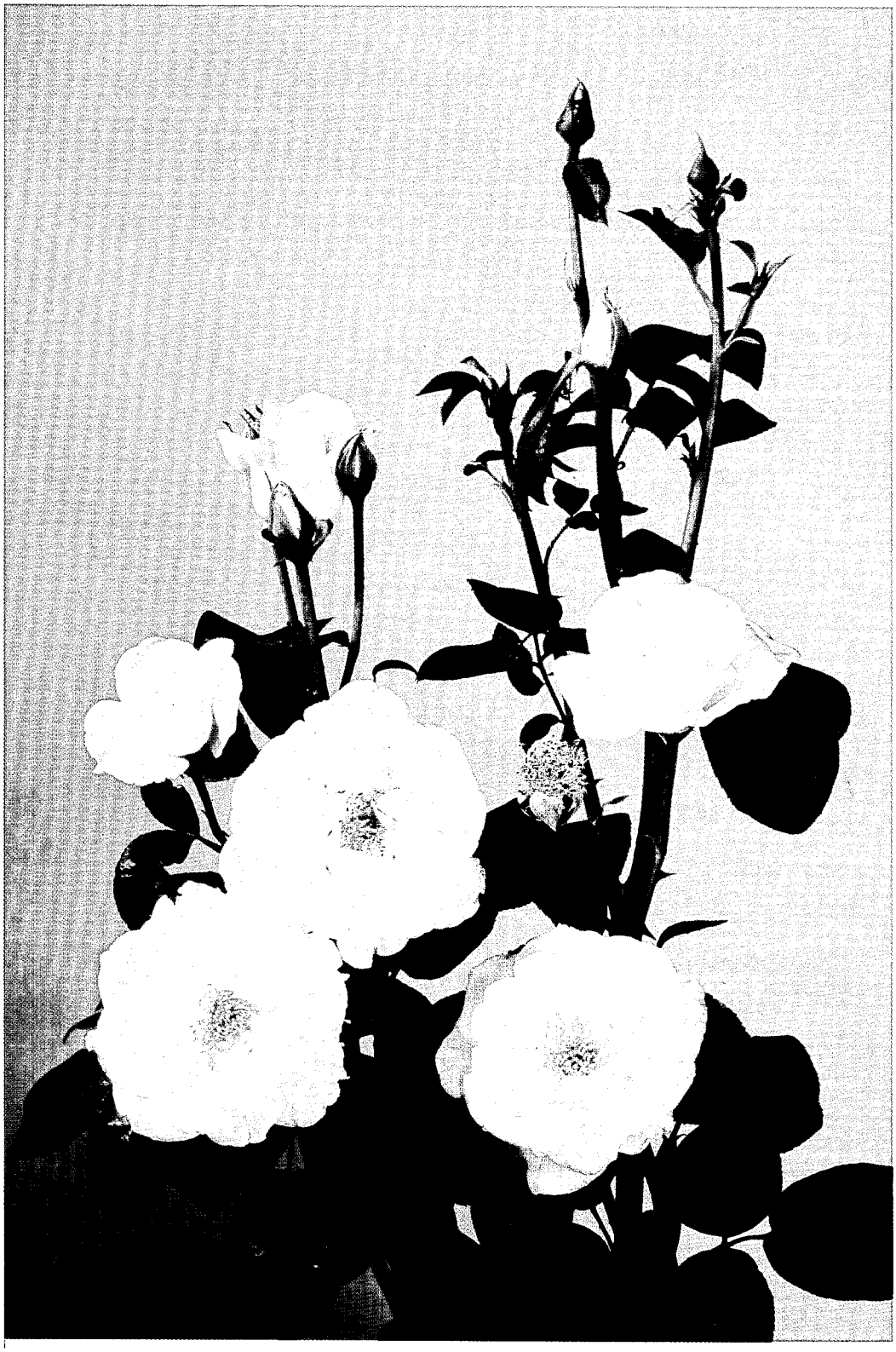

United States Patent

Plant Pat. 3,983

Patented Nov. 23, 1976

3,983

ROSE PLANT

David L. Armstrong, Orange, Calif., assignor to Armstrong Nurseries, Inc., Ontario, Calif.

Filed Nov. 18, 1975, Ser. No. 633,033

Int. Cl. [2] A01H 5/00

U.S. Cl. Plt.—14 1 Claim

ABSTRACT OF THE DISCLOSURE

A hybrid tea rose having foliage which displays a somewhat greater resistance to mildew than comparable varieties raised under parallel conditions. Light yellowish white buds open to white blooms from 3¾ to 4½ inches in diameter. Flower longevity in September, where plants are grown outdoors, is from two to three days on the bush, and from three to four days after cutting, if kept indoors at living-room temperatures. The flower has moderate fragrance and is characterized in the fact that it is almost entirely white in color, with very subtle golden yellow shading. It has about 160 stigmas. Preliminary experience with this variety in production indicates that it tends to grade out better than comparable roses of similar varieties, under parallel conditions.

This invention relates to a new variety of hybrid tea rose which is a tall bush plant. It was grown as a seedling for outdoor use, primarily in garden decoration. It was invented by David L. Armstrong, and hybridized in Ontario, Calif. The seed parent was "Mount Shasta," PP 2,132, and the pollen parent was "Matterhorn," PP 2,688. The variety holds its distinguishing characteristics through succeeding propogations by budding.

The stems are strong and of medium length. Sometimes they bear the flowers singly, but more often in irregular clusters of from 2 to 5 blooms. The quantity of bloom is abundant on the outdoor plants, and it is nearly continuous during the growing season. There is a slight to moderate tea rose fragrance.

The new cultivar may be distinguished from its seed parent, Mount Shasta, most especially in the fact that whereas Mount Shasta has only 20 to 26 petals, the new cultivar has flowers with 35 to 45 petals, plus 5 to 10 petaloids. Furthermore, the flowers of the new cultivar have a smaller range of size than the blooms of Mount Shasta. The latter range from 4½ to 5 inches in diameter, whereas the new cultivar ranges from 3¾ to 4½ inches.

The same difference is noted in comparing the new cultivar with its pollen parent, Matterhorn. That is to say, the flowers on the new cultivar range through a smaller diameter than those on Matterhorn, which are of about the same size generally as the blooms on Mount Shasta. The plant, although tall, is not nearly as high growing as the very tall pollen parent Matterhorn. Stigmas are found in the new cultivar to the number of about 160. This is twice as many as are usually found in the flowers of the pollen parent Matterhorn.

A distinguishing characteristic of the new cultivar is its apparent capacity to "grade out," with a higher percentage of No. 1 plants [1] than Matterhorn.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

[1] Standards of American Rose Society.

BUD

The peduncle is of average length and from average to heavy in caliper. It is erect and has numerous stipitate glands and numerous hairs. The color is near Strong Yellow Green, 5GY6/8.

Before the calyx breaks, the bud is medium in size, of medium length, pointed and ovoid, with a conspicuous neck. Sometimes there are foliaceous parts extending beyond the tip of the bud for a distance equal to one-fourth or more of its length.

As the calyx breaks, the color is near Brilliant Yellow Green, 2.5GY9/8. The inner surface of the sepals carries a fine tomentum. Margins of sepals which developed on the outer surface and the outer surfaces of all sepals have numerous stipitate glands and hairs.

As the first petal opens, the size of the bud is average, and it is long and ovoid to urn-shaped in form. The color on the outside of the petal is near Brilliant Yellow Green, 2.5GY9/8, near the base, while the remainder is between this color and white. The inside surface of the petal shows near Brilliant Greenish Yellow, 10Y9/9, at the base, while the remainder is between this color and white. The bud opens up well and is not prevented from opening by cold, hot, wet, or dry weather.

BLOOM

The size of the bloom when fully open is average, being from 3¾ to 4½ inches in diameter. The petalage is double, with from 35 to 45 petals arranged irregularly, plus 5 to 10 petaloids. The bloom is cupped at first, becoming flat to cupped. The petals are at first somewhat loosely cupped, becoming later, at maturity, more loosely cupped, with tips reflexed slightly outward.

The petals are of medium thickness and moderately leathery, with inside shiny to satiny, while the outside is slightly shiny to satiny. The outside petals are broadly obovate, while the intermediate petals are obovate. The inside petals vary from narrowly obovate to regularly obovate, to irregular. The colors may be modified by being striped, blotched, shaded and/or washed with other colors.

The paragraph immediately following describes color values observed in a flower newly opened in the month of September. The plant had been grown outdoors, in Ontario, Calif.

The outer surface of the outside petal was near Brilliant Greenish Yellow, 10Y9/9, at a small area at the base, the remainder being between this color and white. The inner surface was essentially the same coloring as the outside. The intermediate petals as well as the inner petals, both on the inner surface and the outer surface, were of essentially the same coloration as the outside petals.

The following paragraph describes the color values observed in a bloom which had been open for three days, outdoors, in the month of September. The plant had been grown outdoors in Ontario, Calif.

The coloring of the bloom was essentially the same as for the newly opened flower, the outer surface of the outside petal having a small area at the base which was near Brilliant Greenish Yellow, 10Y9/9, with the remainder between this color and white. The inner surface of the outside petal was essentially the same, except there appeared to be slightly less yellow tint toward the margins which was not measurable with the Nickerson Color Fan. Both the outer surface and the inner surface of the inside petal remained essentially the same as the corresponding part on the newly opened flower.

The general color effect of the newly opened flower was off-white, with a creamy pale yellow tint. After being three days open, the bloom was off-white. The petals drop off cleanly, except for petaloids, and are not particularly affected in this respect by cold, hot, wet, or dry weather.

The flower on the bush in the garden persists for from 2 to 3 days in the month of September, in the locality named. Cut roses grown outdoors and kept at living-room temperatures will last from 3 to 4 days in the month of September.

REPRODUCTIVE ORGANS

Stamens

The stamens are average in number and arranged regularly about the pistils, a few being mixed with petaloids.

Filaments

The filaments are from medium length to long, being 10 to 17 mm. in length. The color is variable: Filaments toward the inside are near Deep Purplish Pink, 7.5RP6/12, in color, while those around the outer perimenter are near, but lighter than, Brilliant Greenish Yellow, 7.5Y9/8. Most are with anthers.

Anthers

The anthers are of medium size, opening at various times. Along the margins of the upper side, the color is near Moderate Orange Yellow, 7.5YR8/8. In the mid-portion, the color of both the under side and the upper side is lighter than Brilliant Greenish Yellow, 7.5Y9/8.

Pollen

Pollen is moderate, and near Strong Orange Yellow, 7.5YR7/11, in color.

Pistils

The pistils are from average to many in number, approximately 160.

Styles

The styles are uneven, of average length and caliper, and loosely bunched. The color is near Strong Red, 2.5R/12, just below the stigmas, and becoming near Brilliant Yellow Green, 2.5GY8/9, closer to the ovaries.

Stigma

The stigma is between Light Yellowish Pink, 2.5YR9/3, and Moderate Yellowish Pink, 10R8/6, in color.

Ovaries

Most of the ovaries are enclosed in the calyx.

Hips

The hips are of average length and globular in form, with smooth, thick and fleshy walls. At one-half the mature stage, the color is near Strong Yellow Green, 5GY6/8, covered with a gray bloom.

Sepals

The sepals are permanent. They are medium-length and recurved. The inside coloration is between Dark Greenish Yellow, 10Y6/7, and Strong Brown, 2.5YR4/7, heavily overlaid with grayish tomentum. The outside coloration is between Moderate Yellow Green, 2.5GY5/5, and Strong Brown, 5YR4/5.

Seeds

There are few to average number of seeds, from 8 to 12 in number, and these range from small to medium in size.

FOLIAGE

The compound leaves usually comprise three to seven leaflets, which are normal in quantity, from medium size to large, heavy, leathery, and semi-glossy. The leaflets are broadly ovate, with apex acute, base obtuse, and margin irregularly serrate.

The mature foliage displays upon its upper surface a color which is between Moderate Olive Green, 5GY4/3, and Grayish Olive Green, 5GY3/2, covered with a light gray bloom. The under surface is near Moderate Yellow Green, 5GY5/6, in color, and covered with a gray bloom.

The young foliage, on its upper surface, is near Moderate Yellow Green, 5GY5/6, in color, lightly to moderately overlaid with near Dark Red, 2.5R3/7. The under surface is near Strong Yellow Green, 7.5GY6/8, in color, also lightly to moderately overlaid with near Dark Red, 2.5R3/7.

The rachis is average to heavy in size, grooved on the upper side, with some stipitate glands on the edges. The under side is sparsely prickly, with stipitate glands.

The stipules are moderately short and medium-width, with medium-length points turning out at an angle of less than 90°.

The plant displays a more than average resistance to mildew, when compared to other varieties currently in commerce grown under similar conditions.

GROWTH

In habit, the plant is bushy and upright, and moderately branched. It displays a moderately vigorous growth. The canes are from medium to heavy in caliper.

The main stems are between Light Olive, 10Y5/5, and Light Olive, 5Y5/6, in color, with a light bloom. They bear several large prickles, which are medium-length to long, and from almost straight to hooked slightly downward, with short to medium-length moderately broad bases. Their color is from gray to a light brown near Moderate Orange Yellow, 7.5YR8/8. There are a few small prickles, and their color is the same as that of the large prickles. There are no hairs.

The branches are between Moderate Yellow Green, 2.5GY5/5, and Light Olive, 10Y5/5, in color, and covered with a light grayish bloom. They carry from few to several large prickles, which are medium-length, hooked slightly downward, with short moderately broad bases. Their color is between Moderate Orange Yellow, 7.5YR-8/8, and Moderate Brown, 7.5YR4/5. There are few small prickles, which are the same color as the large prickles. There are no hairs.

New shoots are near Light Olive, 10Y5/5, in color, and lightly overlaid with a color near Dark Red, 2.5R3/7, and covered with a light grayish bloom. There are very few large prickles, and these are medium-length and from almost straight to hooked slightly downward, with short, moderately narrow bases. There are from none to few small prickles. The color of both the large and small prickles is the same as the color of the new shoots. There are no hairs, and from none to very few stipitate glands.

I claim:

1. A few and distinct variety of hybrid tea rose, substantially as described and illustrated herein, and having, in combination, a tall upright moderately branched habit of growth with medium to heavy caliper canes, and foliage which is characterized in that it is slightly more resistant to mildew, on the average, than plants of a similar variety grown under parallel conditions, said rose plant further bearing buds of a light yellowish white color which open to blooms ranging from 3¾ to 4½ inches in diameter which have from 35 to 45 petals, plus 5 to 10 petaloids, and about 160 stigmas, the variety further being characterized in that a row of such plants tends to yield a higher proportion of No. 1 plants than does a row of comparable varieties.

No references cited.

ROBERT E. BAGWILL, Primary Examiner